US009663553B2

(12) United States Patent
Vadde et al.

(10) Patent No.: US 9,663,553 B2
(45) Date of Patent: May 30, 2017

(54) INTEGRATED PROCESS FOR THE PRODUCTION OF THERAPEUTICS (HUMAN ALBUMIN, IMMUNOGLOBULINS, CLOTTING FACTOR VIII AND CLOTTING FACTOR IX) FROM HUMAN PLASMA

(71) Applicant: HEMARUS THERAPEUTICS LIMITED, Hyderabad (IN)

(72) Inventors: Neelima Vadde, Hyderabad (IN); Mitali Samaddar, Hyderabad (IN); Ashok Nuvula, Hyderabad (IN); Zinia Chakraborty, Hyderabad (IN); Swapna Sagar Duggineni, Hyderabad (IN); Uma Devi Komath, Hyderabad (IN)

(73) Assignee: HEMARUS THERAPEUTICS LIMITED, Hyderabad (IN)

( * ) Notice: Subject to any disclaimer, the term of this patent is extended or adjusted under 35 U.S.C. 154(b) by 0 days.

(21) Appl. No.: 14/530,840

(22) Filed: Nov. 3, 2014

(65) Prior Publication Data
US 2015/0210737 A1   Jul. 30, 2015

(30) Foreign Application Priority Data
Jan. 29, 2014   (IN) .............................. 378/CHE/2014

(51) Int. Cl.
*A61K 38/00*   (2006.01)
*C07K 1/36*   (2006.01)
*C07K 1/18*   (2006.01)
*C12N 9/64*   (2006.01)
*B01D 15/34*   (2006.01)
*B01D 15/36*   (2006.01)
*B01D 15/38*   (2006.01)

(52) U.S. Cl.
CPC ............... *C07K 1/36* (2013.01); *B01D 15/34* (2013.01); *B01D 15/362* (2013.01); *B01D 15/363* (2013.01); *B01D 15/3804* (2013.01); *B01D 15/3828* (2013.01); *C07K 1/18* (2013.01); *C12N 9/644* (2013.01); *Y02P 20/125* (2015.11)

(58) Field of Classification Search
None
See application file for complete search history.

(56) References Cited

U.S. PATENT DOCUMENTS

| | | |
|---|---|---|
| 2,390,074 A | 12/1945 | Cohn |
| 4,093,608 A | 6/1978 | Iga et al. |
| 4,228,154 A | 10/1980 | Fisher et al. |
| 4,371,520 A | 2/1983 | Uemura et al. |
| 4,639,513 A | 1/1987 | Hou et al. |
| 4,675,384 A | 6/1987 | Dromard et al. |
| 4,822,872 A | 4/1989 | Kameyama et al. |
| 4,877,866 A | 10/1989 | Rudnick et al. |
| 5,061,789 A | 10/1991 | Moller et al. |
| 5,138,034 A | 8/1992 | Uemura et al. |
| 5,245,014 A | 9/1993 | Kaersgaard |
| 5,286,849 A | 2/1994 | Herring |
| 5,346,992 A | 9/1994 | Grandgeorge et al. |
| 5,378,365 A * | 1/1995 | Arrighi ................ C07K 14/745 210/635 |
| 5,457,181 A | 10/1995 | Michalski et al. |
| 5,614,500 A | 3/1997 | Zimmermann |
| 5,639,857 A | 6/1997 | Zimmermann |
| 5,677,424 A | 10/1997 | Rucheton |
| 5,679,776 A | 10/1997 | Burnouf-Radosevich et al. |
| 5,714,583 A | 2/1998 | Foster et al. |
| 6,063,909 A | 5/2000 | Huang et al. |
| 6,258,938 B1 | 7/2001 | Furie et al. |
| 6,893,639 B2 | 5/2005 | Levy et al. |
| 7,041,798 B1 | 5/2006 | Kothe et al. |
| 8,088,416 B2 | 1/2012 | Jorquera Nieto et al. |
| 2001/0051708 A1 | 12/2001 | Laursen et al. |
| 2004/0106779 A1 | 6/2004 | Bigler et al. |
| 2007/0049733 A1 | 3/2007 | Zurlo et al. |
| 2007/0299251 A1* | 12/2007 | Lihme ...................... C07K 1/16 530/416 |

FOREIGN PATENT DOCUMENTS

| | | |
|---|---|---|
| DE | 3640513 C2 | 11/1990 |
| EP | 617049 B1 | 9/1994 |
| WO | 9429334 | 12/1994 |
| WO | 98/05686 | 2/1998 |
| WO | 2006023831 A2 | 3/2006 |

(Continued)

OTHER PUBLICATIONS

Burnouf et al., (J. Biochem. Biophys., vol. 49, 2001, pp. 575-586).*
Tan et al. ( J. Biomed. & Biotechnol, vol. 2009, pp. 1-10, Nov. 2009).*
Cohn, E.J., L.E. Strong, W.L. Hughes,Jr., D.J. Mulford, J.N. Ashworth, M. Melin, H.L. Taylor, J. Am. Chem. Soc., 1946, 459-475, 68.
Cohn, E.J., et al, J. Am. Chem. Soc., 1950, 465-474, 72.
J. Curling, Integrating new technology into blood plasma fractionation, BioPharm Sep. 2002, 16-25.
Adil Denizli, Plasma Fractionation: conventional and chromatographic methods for albumin purification J. Biol. Chem., 2011,315, 341, 39(4).

(Continued)

*Primary Examiner* — Hope Robinson
(74) *Attorney, Agent, or Firm* — Harita S Achanta (57) ABSTRACT

The invention is an integrated process for the isolation and purification of plasma derived clotting Factor VIII, clotting Factor IX, albumin and immunoglobulin without the use of ethanol precipitation. The integrated process comprises of sequential chromatography steps of gel filtration, anion exchange and cation exchange chromatographies, followed by viral inactivation and removal steps. The present invention has the advantage of being a mild process that does not denature or aggregate the proteins and provides high yields of several therapeutic grade plasma proteins from a given volume of plasma.

6 Claims, 10 Drawing Sheets

(56) References Cited

FOREIGN PATENT DOCUMENTS

| WO | 2007063129 | 6/2007 |
|---|---|---|
| WO | 2007136327 | 11/2007 |

OTHER PUBLICATIONS

Patrick Robert, Pharmaceuticals Policy and Law, 2009, 359-367, 11.
Patrick Robert, Worldwide supply and demand of plasma and plasma-derived medicines, Iranian J. of Blood and Cancer, 2011, 111-116, vol. 3, No. 3.
Farrugia A., Plasma for Fractionation: Safety and Quality Issues. Haemophilia, 2004, 334-340, 10.
Braz. J. Med. Biol. Res., 1998, 1383-1388, 31.
Braz. J. Med. Biol. Res., 1998, 1375-1381, 31.
Lontos, J., Plasma Product Biotech meet, http://www.bo-conf.com/ppb05/present/ppt.htm 2005.
Bertolini, J., Davies, J., Wu, J., Coppola, G., Purification of Immunoglobulins, 1998.
Dr. Jean-Francois Prost, "Will plasma products inevitably be replaced by a new generation of therapeutics?", Plasma Product Biotechnology meet 2011.

\* cited by examiner

FIG. 1: An outline illustration of integrated process scheme for simultaneous purification of four different plasma products without the use of an ethanol precipitation step.

FIG. 2: Zone Electrophoresis of IgG and Albumin

1. IgG BRP Standard
2. IgG Purified
3. IgG Ref. Standard
4. Albumin BRP standard
5. Albumin In-house sample 1
6. Albumin In-house sample 2
7. Albumin Standard

FIG. 3A: HPLC analysis of IVIG

Purified IVIG

Market Comparator – Reference

FIG. 3B: HPLC analysis of Albumin

Purified albumin

Market Comparator – Reference

FIG. 4: Table 1: Test for impurities in Factor IX preparation

| Test | Specification as per Pharmacopoeia | Results |
|---|---|---|
| Activity of factor II | Not more than 5% of the activity of Factor IX | 0.798% |
| Activity of factor VII | Not more than 5% of the activity of Factor IX | 0.09% |
| Activity of factor X | Not more than 5% of the activity of Factor IX | 0.306% |
| Heparin | The preparation to be examined contains not more than 0.5 IU of heparin per International Unit of Factor IX | 0.0095 IU of heparin per International Unit of Factor IX |

FIG. 5: Table 2: Summary of few major test results for purified IVIG

| | TEST | SPECIFICATION | RESULTS |
|---|---|---|---|
| 1 | Protein composition by Zone Electrophoresis | IgG : ≥ 96%<br>Other proteins : ≤ 4% | IgG: 100% |
| 2 | Distribution of molecular size by HPLC | Retention time<br>RRT to the corresponding peak in the chromatogram obtained with the reference solution should be 1±0.02 | RRT for Monomer: 1.001 |
| 3 | Anticomplementary activity | Consumption of complement : ≤ 50 per cent (1 CH50 per mg of Ig) | Consumption of complement : 19.9 per cent (0.34 CH50/mg of Ig) |
| 4 | Prekallikrein activator | ≤ 35 IU/ml | 7.434 IU/ml |
| 5 | Anti-A and Anti-B haemagglutinins | The 1 to 64 dilutions do not show agglutination | No agglutination observed |
| 6 | Anti-D antibodies | The titre of the preparation to be examined should not be greater than the titre of the reference preparation | The titer of the test preparation < titer of the reference preparation (1/4 dilution) |
| 7 | Antibody to hepatitis B surface antigen | ≥ 0.5 IU/g of IgG | 58.306 IU/g of IgG |
| 8 | Immunoglobulin A | ≤ 4 mg/L | 0.5 mg/L |
| 9 | IgM | ≤ 0.1 mg/Ml | 0.000009 mg/mL |
| 10 | Test for viral and bacterial antibodies | a) Antibodies to Viral Antigens; Antibodies to Hepatitis B surface antigen | Conc. of Viral/ Bacterial antibodies: ≥3 times that in the initial pooled material. | The conc. of Abs to HBsAg is 6.0 times than that in the initial pooled plasma |
| | | b) Antibodies to Bacterial Antigens; Antibodies to Diptheria Toxoid antigen | | The conc. of Abs to Diptheria toxoid is 11.2 times than that in the initial pooled plasma |
| 11 | Test for Fc function of Immunoglobulin | IFc: ≥60% (Stated for EP. Ref std, Human immunoglobulin BRP batch 3) | IFc = 78.79% |

FIG. 6: Table 3: IgG Subclass distribution for different Batches

| IgG Subclasses | Specification | Market Comparator | Batch XXX-- | Batch XXX-- | Batch XXX-- |
|---|---|---|---|---|---|
| IgG1 | 63%-69 % | 61.9 | 66.70% | 66.84% | 67.99% |
| IgG2 | 23.8%-31% | 33.1 | 27.86% | 28.17% | 24.50% |
| IgG3 | 2.9%-5.8 % | 3.6 | 4.09% | 3.40% | 3.84% |
| IgG4 | 1.4%-2.9 % | 1.4 | 1.55% | 1.59% | 1.67% |

FIG. 7: Table 4: IgG – Process or source related impurities for different batches

| Test | Specification | Market Comparator | Batch-*1 | Batch-*2 | Batch-***3 |
|---|---|---|---|---|---|
| Prekallikrein activator IU/ml | ≤ 35 | 8.5 | 6.79 | 6.41 | 6.78 |
| Ig A mg/L | ≤ 4 | 3.7 | 0.3 | 0.5 | 0.2 |
| Ig M mg/mL | ≤ 0.1 | 0.0391 | 0.000009 | 0.000011 | 0.000010 |

FIG. 8: Table 5: Levels of Pre-kallilkrein activator in albumin preparations in two representative batches

| Test | Specification | RD/ALxy/yyy | PS/ALxy/zzz |
|---|---|---|---|
| Prekallikrein activator | ≤ 35 IU/mL | 1.637 IU/ mL | 2.646 IU/mL |

FIG. 9: Table 6: Summary of exemplary Quality Control tests for impurities in purified Albumin preparation

| TEST | SPECIFICATION | RESULTS |
|---|---|---|
| Protein composition by Zone Electrophoresis | Albumin : 96% minimum Other proteins : 4% maximum | Albumin:100% |
| Molecular size distribution by HPLC | 5% (w/v) maximum aggregate protein. | % Monomer: 99.749 |
| | | % High molecular weight: 0.251% |
| Haem by absorption at 403 nm | $A_{403}$ : ≤ 0.15 | 0.045 |
| Prekallikrein activator | ≤ 35 IU/ml | 2.646 IU/ml |
| Aluminum (Atomic absorption spectrometry) | ≤ 200 µg/L | Not detected (LLD = 10µg/L) |
| Potassium (Atomic emission spectrometry) | ≤ 0.05 mmol of K per g of protein | Not detected (LLD = 0.00002 mmol per g of protein) |
| Sodium (Atomic emission spectrometry) | 145 ± 15 mmol/L | 147.65 mmol/L |
| Alkaline Phosphatase | Maximum 0.1 Unit per g of protein | 0.0146 Units /g of protein |

INTEGRATED PROCESS FOR THE PRODUCTION OF THERAPEUTICS (HUMAN ALBUMIN, IMMUNOGLOBULINS, CLOTTING FACTOR VIII AND CLOTTING FACTOR IX) FROM HUMAN PLASMA

BACKGROUND OF THE INVENTION

1. Field of the Invention

The invention relates to the methods to manufacture through fractionation and purification of human albumin, immunoglobulins, clotting Factor VIII and clotting Factor IX, from human plasma by sequential chromatography steps to produce highly pure, virus-free and therapeutically administrable proteins. The purification is carried out by an all-chromatography process that avoids the use of ethanol precipitation.

2. Background Art

The first reported plasma fractionation process for therapeutic purposes was developed about 60 years ago by Cohn and co-workers (J. Am. Chem. Soc., 68, 459-475, 1946; J. Am. Soc. 72, 465-474, 1950). Since then, plasma fractionation industry has grown mani-fold and is now one of the largest industry segments in global therapeutic protein manufacture (J. Curling, Integrating new technology into blood plasma fractionation BioPharm September 2002, 16-25; Adil Denizli, Plasma Fractionation: conventional and chromatographic methods for albumin purification J. Biol. Chem., 39(4), 315, 341, 2011).

Plasma protein fractionation is approximately an 11.8 billion dollar industry (Plasma Product Biotechnology meet 2011, Dr. Jean-Francois Prost, "Will plasma products inevitably be replaced by a new generation of therapeutics?") supplying products to more than a million patients each year. It is estimated that more than 500 metric tons of human serum albumin and more than 40 tons of intravenous immunoglobulin are produced annually from more than 22 million liters of source and recovered plasma. Plasma contains about 60 g/L of protein, of which about 57 grams (not including processing losses) are used for many therapeutic products. Plasma-derived products, such as IVIG and albumin, are not expected to be manufactured by recombinant means. IVIG demand is now the primary driver of the plasma collection market, with demand growing 6-8% annually.

According to a market report published by Robert, P. in Pharmaceuticals Policy and Law 11, 359-367, 2009, the demand for plasma in the 1950s and 60s was driven by the demand for human albumin. In the late 1960s, when Factor VIII concentrates became available, the global plasma requirement was driven by the growing demand for clotting factors. The IVIG usage has grown significantly in different medical areas such as neurology, rheumatology, nephrology, dermatology, oncology and infectious diseases, as well as allergy and immunology, in addition to the continuing increase of the number of patients with primary immune deficiencies. Based on this usage pattern, which characterizes the markets in most industrialized countries, the volume of IVIG was forecast to grow from about 82.3 metric tons in 2008 to about 107.9 tons by 2012, corresponding to an annual growth rate of 7%—the rate observed in the past ten years. According to this report, the demand of IVIG beyond 2012, is expected to grow depending upon the results of the Alzheimer's disease trials and the possible approval of IVIG for this new indication.

In 2010, there were a total of 78 fractionation plants operating in the world, with 25 of them in China, 26 in Europe and 8 in United States (Worldwide supply and demand of plasma and plasma-derived medicines, Patrick Robert, Iranian J. of Blood and Cancer, Vol. 3, No. 3, 111-116, 2011). The global fractionation capacity was estimated at about 48.4 million liters, producing mainly albumin, polyvalent IVIG, Factor VIII, Factor IX and Hyperimmunes. Hemophiliacs are the target population for players interested in plasma protein R&D. India needs about 900,000 liters of plasma derived proteins per year. India has been meeting this requirement so far by importing these proteins as the plasma fractionation industry is still at a nascent stage, one of the major hindrances being the existence of adequate infrastructure for plasma collection (Farrugia A., Plasma for Fractionation: Safety and Quality Issues. Haemophilia 10, 2004: 334-340).

Although the number of plasma fractionators are growing and global capacities are increasing, so is the demand for IVIG growing, which is projected at about 7% to 13% annually between 2012 and 2015. To meet this demand, more raw plasma will need to be dedicated to immunoglobulin purification, along with improvements in the process that will increase the overall IVIG yield. This growing requirement for IVIG will limit the availability of plasma for the manufacture of new plasma-derived blood products unless their manufacture is integrated into the existing manufacturing processes for plasma-derived products such as immunoglobulins and albumin. Presently, although plasma based therapeutics are safe, efficacious and available, the cost of therapy remains a barrier for access to the drugs. This can be addressed only if human plasma, a uniquely rich starting material for therapeutic proteins, can be processed to prepare several more therapeutic proteins besides the conventional albumin, IVIG and clotting factor concentrates. This also requires the use of more discerning technologies of bioprocess operations like chromatography and membrane separations together with the most recent and proven methods of viral inactivation.

Plasma being a scarce and exclusive commodity, there is a continuous need to upgrade the fractionation processes so as to maximally utilize this valuable resource. By continuously refining and upgrading the existing processes and improving process efficiencies, the market availability status and the quality of the end products can be improved. The fractionation industry which presently uses either a Cohn or a modified Cohn's method of ethanol precipitation in some cases may use chromatography based purification in the subsequent steps. Cohn's fractionation limits the number of proteins that can be purified by ethanol precipitation as only the more abundant proteins from plasma can be precipitated by this method. The less abundant therapeutic proteins with good therapeutic potential need to be processed using a different strategy. It's also now accepted in the plasma fractionation industry that although Cohn's method permits fractionation of large volumes of plasma at low cost, the quality of the product obtained by chromatography is superior (Braz. J. Med. Biol. Res., 31:1383-1388, 1998). Several companies have now moved to usage of a combination of both methods, where they have ethanol precipitation followed by chromatography. The inherent disadvantage in this method is the possibility of protein denaturation and/or aggregation during the addition of ethanol (Braz. J Med Biol Res, 31: 1375-1381, 1998). Protein losses may also occur in the supernatant after ethanol precipitation thereby decreasing the overall recovery of major proteins and almost a total loss of the minor proteins. The concentration of different proteins in the plasma varies over a very wide range, from less than 1 microgram per ml to 40 grams per liter. To develop separation and purification processes that can ensure production of several of these high and low level proteins from the same starting volume of plasma, is a challenge for the separation specialists.

There are several patents in the prior art that disclose a process for fractionation and/or purification of plasma proteins to therapeutic grade purity, that involved the use of ethanol for initial precipitation, followed by chromatography steps with few technologies involving only chromatographic steps or only ethanol precipitation steps.

Preparation of a high-purity human Factor IX concentrate and other plasma proteins and their therapeutic use with chromatography process were discussed in U.S. Pat. No. 5,457,181. U.S. Pat. No. 4,371,520 discloses a process for preparing immunoglobulin suitable for intravenous injection, comprising treatment of an acid a plasma or combination of fractions I, II and III, combination of fractions II and III, fraction II, or fraction III obtained from plasma by Cohn's cold alcohol fractionation and chromatography methods. Process for the isolation and/or fractionation of peptide, 5 polypeptides or protein solutions discussed in WO200763129, involves both chromatographic steps and ethanol precipitation steps. Patent application WO200623831 relates to chromatographic methods for recovering highly purified proteins sequentially from biological samples. U.S. Pat. No. 5,679,776 discloses a simple chromatographic process for purifying Factor VIII from total plasma. However, none of the above referred patents discloses a process that can simultaneously isolate and purify several proteins from the same starting volume from human plasma to therapeutic grade proteins by avoiding the use of ethanol precipitation step anywhere in the process.

Another patent, U.S. Pat. No. 7,041,798 discloses a method for the chromatographic fractionation and ethanol precipitation of plasma and serum preparations, and relates to the fractionation of plasma or serum into albumin and immunoglobulin by hydrophobic interaction chromatography. The rate limiting step is the processing time associated with starting material which can be challenging at large scale.

Patent U.S. Pat. No. 4,639,513 discloses a method for producing intravenously injectable immunoglobulin G (IgG) comprising a particulate separation step, an ion exchange separation step and an affinity separation step, ethanol precipitation, additionally useful high purity by-products such as prothrombin complex, transferrin and albumin recovery, were published. However, these methods often employ a separation medium that can be designed to selectively adhere either the protein of interest or the impurities.

Patents U.S. Pat. No. 4,877,866 and DE 3640513C2 disclose the methods appropriate for industrial-scale production and multistage purification of plasma that contains immunoglobulin G accompanied by treatment with ultrafiltration and ethanol precipitation. However, a need exists for an efficient process for purifying an immune serum globulin fraction from a crude plasma protein fraction.

The patent application WO1994029334 discloses chromatographic and ethanol precipitation steps to produce therapeutic quality of the IVIG. However, the claimed method fails to take the subsequent purification of albumin into account.

Although a number of chromatography based processes have been described in research publications for the production of IVIG without the use of ethanol precipitation, but at the industrial scale, an all-chromatography process scheme has just begun gaining acceptance due to the better quality of the final IVIG product (lesser protein denaturation and aggregation) and better yields (Lontos, J., Chromatographic purification of immunoglobulins at CSL bioplasma; a manufacturing perspective. Plasma Product Biotech meet, www.bo-conf.com/ppb05/present/ppt.htm 2005; Bertolini, J., Davies, J., Wu, J., Coppola, G., Purification of Immunoglobulins. 1998, WO 98/05686; Ultra-high yield intravenous immune globulin preparation, Zurlo, E. J., Curtin, D. D., Louderback, A. L., US patent application US20070049733A1).

Several patents have explored the use of chromatographic methods for the final purification steps particularly ion exchange chromatography. A few patents have also tried to replace the ethanol fractionation of plasma with caprylate or citrate precipitation steps followed by chromatography based clean-up steps for purification. In spite of these advancements, it is glaringly apparent how Cohn's fractions II and III continue to play an important role as the starting material for IVIG purification in most industrial processes. This is clearly evident in a patent being granted (U.S. Pat. No. 6,893,639 B2) to an ethanol based plasma fractionation process at sub-zero temperatures, as recent as 2005 (the initial Cohn's patent for ethanol based plasma fractionation U.S. Pat. No. 2,390,074, was granted in 1945). Cohn himself had illustrated the problems of protein denaturation as an undesirable outcome of ethanol precipitation.

Similar issues are applicable for human albumin as well. The industrial processes for purifying albumin start with Fraction V of ethanol fractionation of plasma by the Cohn's method (J. Am. Chem. Soc. 1946, 68, 459-475, Cohn et al.). Although ethanol fraction supernatants of fraction IV and even supernatants of fractions II & Ill have been used by several manufacturers for albumin purification, followed by chromatography steps, a complete all-chromatography process has not been the norm in the industry for albumin purification (U.S. Pat. No. 5,346,992 and U.S. Pat. No. 4,288,154). Chromatography techniques for albumin purification in research publications and books have been cited since the 1980s (Curling J. M., Methods of plasma protein fractionation, Ed. J. Curling, Acad. Press, 77-91 (1980); Saint-Blancard J., Novel Trisacryl ion exchangers (Nouveaux echangeurs d'ions Trisacryl), Ann. Pharm. Fr. 39, 403-409 (1981)). Patents that claim to purify albumin by chromatography are also seen to use supernatant IV or precipitate V of the Cohn's fraction (U.S. Pat. No. 5,677,424; U.S. Pat. No. 4,675,384; U.S. Pat. No. 4,228,154; U.S. Pat. No. 8,088,416) as the starting material.

U.S. Pat. No. 5,061,789 discloses a method for isolating blood-clotting Factor IX by first adsorbing it onto a matrix derivatised with alpha hydroxylamine groups, eluting the factor and adsorbing it onto a column matrix of sulphated carbohydrates to collect a pure form of Factor IX at high yields. U.S. Pat. No. 5,138,034 discloses a process for isolation of the Factor IX by a sequence of steps involving ethanol precipitation, followed by treatment with an anion exchanger and affinity chromatography. U.S. Pat. No. 5,286,849 discloses the process for purification of Factor IX from an impure protein fraction by the addition of a solvent-detergent solution to inactivate any viral contaminants and purify the Factor IX by chromatography on a sulphated polysaccharide resin. The purified Factor IX by the above method is claimed to have a specific activity of at least 85 units/mg. U.S. Pat. No. 5,457,181 discloses a method for preparing a high purity Factor IX concentrate from the supernatant fraction of cryoprecipitated human plasma. A pre-purification is done with DEAE SEPHADEX® chromatography. The resulting Factor IX has a specific activity of at least 0.5 IU/mg of protein. The purification method comprises at least two successive chromatography steps.

The first step is a DEAE SEPHAROSE® chromatography followed by an affinity on HEPARIN SEPHAROSE™. The elution buffer is a citrate buffer at pH 7.4 adjusted with 0.45M NaCl and supplemented with arginine as a stabiliser for Factor IX activity. U.S. Pat. No. 5,614,500 discloses a method for preparing pharmaceutical compositions comprising the active, highly purified and concentrated Factor IX proteins. The Factor IX proteins are recovered from plasma or recombinant cell culture sources by an immunoaffinity chromatography procedure in the presence of a chelating agent and in the absence of an exogenous non-chelating protease inhibitor. U.S. Pat. No. 5,639,857 discloses a method for recovering active, highly purified and concentrated Vit-K dependent proteins from plasma, concentrate or mixtures of proteins produced by recombinant DNA technology. U.S. Pat. No. 5,714,583 discloses a process for purification of Factor IX by following the steps of anion exchange resin, heparin or heparin like resin followed by a hydroxyl apatite resin. The third eluate can be applied to an immobilised metal-affinity resin to get a fourth eluate that contains purified Factor IX. This process would apply to plasma derived as well as recombinant Factor IX. U.S. Pat. No. 6,063,909 discloses a novel method of protecting blood coagulation Factor IX from proteases during purification or storage was disclosed. Factor IX is stabilized in solution against activation to Factor IX or against degradation to peptides or conformation by the addition of one or more soluble organic or inorganic salts like sodium sulphate, potassium chloride, sodium chloride and/or other salts in the range of 0.7M to 3M, to the Factor IX containing solution. U.S. Pat. No. 6,258,938 discloses a method to isolate the blood clotting Factor IX by using an antibody affinity column that specifically reacts with ligand stabilized protein to be isolated. The antibody to Factor IX is immobilized on to a solid support and a mixture containing the protein in the presence of the ligand is brought in contact with the antibody bound to the column resin. Elution is done under mild conditions to release the protein without the ligand. This gave a protein with a specific activity of at least 125-150 units/mg of protein. They claim that the stability of the purified Factor IX can be improved by the removal of or decreasing the amount of plasma hyaluronan binding protease that may get co-purified with Factor IX according to the invention described in US 20040106779A1. The invention describes the method to decrease the ratio of Factor IX to PHBP by contacting it with an ion exchange column and eluting the protein with 0.35M to 0.4M salt to separate protease from Factor IX.

EP617049 and U.S. Pat. No. 5,378,365 discloses a process for the purification of Factor IX, Factor X and Factor II from human plasma or fractions by chromatographic methods.

Alcohol precipitation and chromatography methods were used in U.S. Pat. No. 4,093,608, which have disclosed a process for separating coagulation Factor VIII from human fresh pooled plasma and purifying it. However, the process is expensive and also lacks specificity.

U.S. Pat. No. 5,245,014 discloses a method for isolating biological compounds such as proteins, especially coagulation Factor VIII in high yield and almost free of other proteins, from body chromatographic and alcohol precipitation methods. However, purity of the obtained Factor VIII seems to be a challenge.

U.S. Pat. No. 4,822,872 discloses a method of purifying an anti-hemophilic factor (AHF) comprising of a cryoprecipitation of Factor VIII and adsorption of the Factor VIII protein on a water insoluble carrier. But, this is a complex process involving the preparation of custom-made resins that is not easy for industrial scale manufacturing. Other patents that discuss isolation and/or purification processes include WO2007136327; US20010051708.

There was hence a requirement, to have an integrated sequential chromatography procedure using regular industrial chromatography resins, to manufacture several products from a given volume of plasma, which ensures maximum utilization of a scarce and precious resource like human plasma and thereby better revenues for the company manufacturing these products.

The present invention discloses an approach to overcome the challenge of utilization of a scarce and precious resource like human plasma, by using a sequential chromatography procedure that can help purify the four proteins Albumin, IgG, and Clotting factors (Factor VIII and Factor IX), with a potential to purify more proteins from the same starting volume of plasma. This will in turn reduce the cost and improve the affordability of these life-saving medicines for the patients.

SUMMARY OF THE INVENTION

The present invention is an improved process for manufacturing plasma proteins using an all-chromatography process. The integrated process scheme simultaneously purifies plasma proteins like Albumin, IgG and clotting factors (Factor VIII and Factor IX), from the same starting volume, thereby reducing the cost, improving affordability and ensuring a more economical process.

BRIEF DESCRIPTION OF THE SEVERAL VIEWS OF THE DRAWINGS

DESCRIPTION OF TABLES

FIG. 5: Table 2: Summary of exemplary test results for purified IVIG

DETAILED DESCRIPTION OF THE INVENTION

Integration of the processes is important to maximally utilize the plasma and recover as many therapeutic products from it as possible with limited resources. Certain combinations of chromatography steps leading to the purification of the individual proteins, starting from the plasma raw material may be available in literature. The present invention discloses an integrated process that involves identification of different products that could be extracted at a particular stage of the process to derive the final product of therapeutic grade purity in minimal steps from the intermediate product. This process involves analysis of the identified intermediates and the suitability of a fraction to be used as starting material to obtain the desired final product.

The present invention has the advantages of minimal duplication of equipment and maximal usage of the facility while purifying the desired products in parallel from a said starting volume of plasma and not sequentially, where purification of product 2 begins after the purification of product 1. In normal purification schemes, the buffer salts are optimised for individual steps for a given product purification scheme. In the present invention, the suitability of the same buffers across the four product purification schemes laterally was also studied and an exercise at minimisation was attempted. This overlap of types of buffers also improves efficiency and economy of the process, thereby minimising the number of salts to be procured for the manufacture of the four products.

Figure 1:
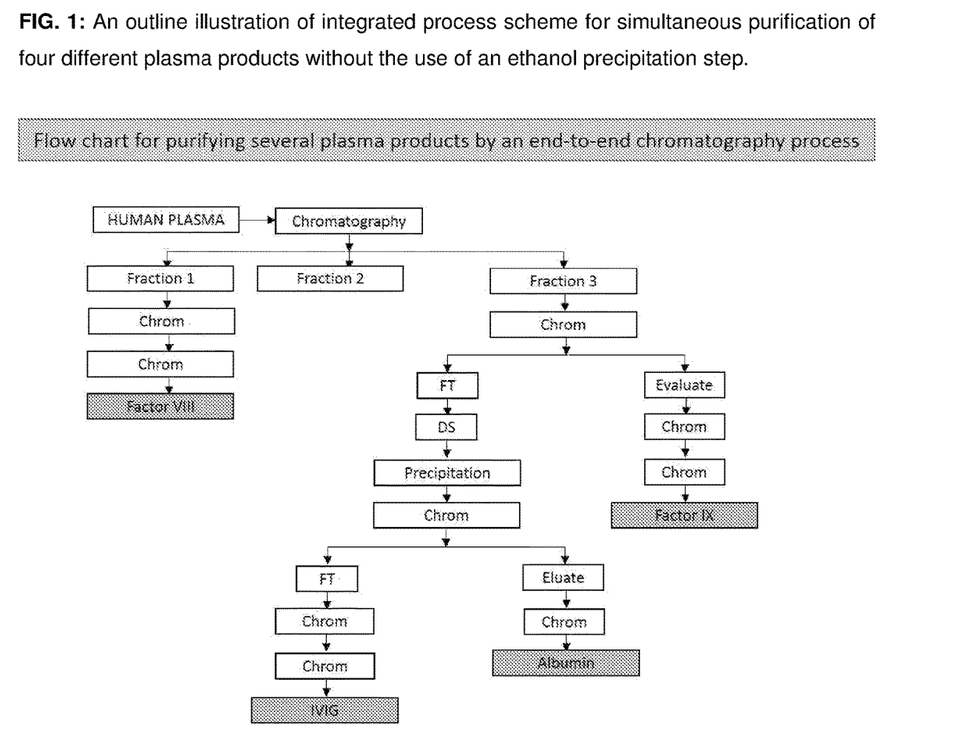
FIG. 1 is an illustration of an integrated process scheme for simultaneous purification of four different plasma products without the use of an ethanol precipitation step.

The invention is schematically described in FIG. 1. The purification scheme shows the preferred embodiment of the sequence of chromatography steps to be followed starting from blood plasma which can be fresh frozen, source plasma, recovered plasma or other variants of liquid or thawed plasma. The characteristic feature is the absence of ethanol precipitation and the simultaneous purification of several plasma proteins to the desired therapeutic grade quality, using an all-chromatography based process.

In the ethanol based fractionation processes such as Cohn's, Cohn-Oncley, and Kistler-Nitschmann processes, when a certain percentage of ethanol is added to plasma for fractionation for the manufacture of IgG or Albumin, several other proteins are irreversibly lost in the supernatant as they get denatured due to the effect of the hydrophobic organic solvent 'ethanol'. In the present invention, a milder non-denaturing method based on a sequence of chromatography steps, is employed. When the plasma is fractionated for the manufacture of IgG or Albumin, other plasma proteins such as Factor VIII, Factor IX, Thrombin, Fibrinogen, Anti-Thrombin-III, A1Pi and C1-INH are available for purification from the intermediate steps in the chromatography sequence, without the need to take a fresh sample of human plasma. This integrated process to manufacture multiple proteins from a given volume of plasma helps optimal utilization of human plasma which is a scarce commodity.

Human plasma is first set to a chromatographic method from which three major fractions of the plasma products are obtained. The said three major fractions are again subjected to product specific sequential chromatographic steps to purify the desired therapeutic proteins such as IVIG, albumin and coagulation Factors IX and VIII.

Fractionation of Plasma:

Plasma is fractionated by separating proteins on a gel filtration column instead of by differential precipitation with ethanol. To achieve this, frozen blood plasma (fresh frozen, source plasma, recovered plasma or other variants of liquid or thawed plasma), the fresh frozen or source plasma is collected by a process called plasmapheresis.

Plasmapheresis involves separation of blood into cellular and other components by any of the standard procedures or by the use of a specialized automated plasma collection system (like Haemonetics PCS-2 or other similar equipments). The automated collection system uses sterile disposable sets in a self-contained automated process that separates the plasma from the cellular blood components that are then returned to the donor. The plasma collected by plasmapheresis is stored frozen below −20° C., preferably below −40° C. in sterile collection bottles.

The production is initiated by thawing the frozen plasma in the bottles and pooling the liquid plasma in an appropriate collection vessel. After filtration, the thawed plasma is loaded onto a gel filtration column. The column is packed with one of the gel filtration matrices such as SEPHAROSE™, although CELLUFINE™, SEPHACRYL™ or other commercial brands having a separation range of 5 kD to 30,000 kD can also be used. The column is packed to a height which is in the range of 30 to 60 cm. The column is run in a buffer composed of phosphate, citrate or other similar buffer salts that give a pH between 6.0 and 7.5. The buffer salt molarity does not exceed 0.2M, preferably less than 150 mM. Additives like NaCl and other salts are added in suitable quantities like 25 mM to 200 mM to preserve the activity of sensitive proteins. After equilibration, the column is loaded with around 50 to 150 liters of thawed plasma which is 15% to 30% column volume. This results in three major fractions (Fraction 1, Fraction 2 and Fraction 3). Fraction 1 contains Factor VIII along with a few other high molecular weight proteins of plasma like IgM and macroglobulins. Fraction 2 contains Fibrinogen along with certain classes of immunoglobulins, lipoproteins, Transferrin and other proteins in this size range. Fraction 3 contains mainly IgG, Albumin, Factor IX, Anti-Thrombin III and several other proteins of medium to smaller molecular size range. The three fractions, Fraction 1, Fraction 2 and Fraction 3 are also referred to as Fraction I, Fraction II and Fraction III interchangeably in different parts of the text.

Purification of Factor VIII

1. The Fraction I collected is further processed using a series of chromatography steps for purifying coagulation Factor VIII using an anion exchange resin packed in a column, the resin is chosen from one of the commercially available anion exchangers like DEAE (diethyl amino ethyl), Q (Quarternary ammonium) or related resins.

Anion exchange column setup:

Salts like acetate, citrate or related salts are used for the equilibration buffer in the molarity range of 0.005M to 0.1M containing salts like NaCl and other salts in the range of 0.01 M to 0.15M at pH in the range of 5.5 to 8.0.

This column is washed with buffer and eluted using an elution buffer in the concentration range of 0.05M to 0.5M containing sodium chloride more specifically in the range of 0.05M to 0.15M. To this buffer of pH 5 to 8.0, sodium chloride is added to a final elution concentration in the range of 0.25M to 2.5M.

2. The anion exchange column step is followed by a solvent-detergent (S/D) treatment for a specified time of less than 12 hrs at room temperature or around 24° C., for virus inactivation. The S/D treated sample is loaded onto a cation exchange column to remove the viral inactivation reagents.

Cation exchange column setup:

The said cation exchange column comprising SP (sulpho propyl) or CM (caboxymethyl) or related resins is eluted with sodium acetate buffer containing 0.1M to 1.5M sodium chloride. The eluate from this column can be optionally loaded onto a gel filtration column containing separation media in the range for high molecular weight separations.

The column can be run using the final formulation buffer. This helps in getting rid of any minor protein impurities in the Factor VIII sample and facilitates exchange of protein into the final formulation buffer.

3. This is subjected to a second virus removal step by nanofiltration using commercially available molecular size cut-off filters followed by a third viral inactivation step after filling the liquid into the vials, freeze drying and then subjecting it to heat treatment at 80° C. for 72 hrs.

An Integrated Process Sequence:

While the collected Fraction 1 is further processed using a series of chromatography steps for purifying coagulation Factor VIII and Fraction 2 can be processed for purifying other plasma proteins such as fibrinogen, Fraction 3 is processed by an interdependent process scheme for purifying Factor IX, Albumin and IgG. The Fraction 3 is loaded on an anion exchange column to obtain two fractions, one fraction containing a mixture of Albumin+IgG while the other fraction contains Factor IX. Euglobulins are removed from the fraction containing Albumin+IgG, by desalting and precipitation. The euglobulin-free plasma fraction containing Albumin+IgG is further loaded on an anion exchange column to separate IgG from Albumin. As each of these chromatography fractions will also contain other plasma proteins such as Anti-Thrombin III, Alpha-1 Proteinase inhibitor, C1-INH, Thrombin and several other therapeutic proteins, different steps can be incorporated to specifically purify each of them without disturbing the purification of the desired set of the four proteins (Albumin, IgG, Factor VIII and Factor IX). The integrated process involves utilizing the eluates and flow-through fractions from the chromatography scheme used for purifying the aforementioned four proteins (Albumin, IgG, Factor VIII, Factor IX) to purify all the other therapeutic proteins present in the sample. The process for the purification of all the proteins is integrated, as they branch away from the primary plasma fractionation step in an inter-dependent manner. For example, the flow through of the first anion exchange column is the starting material for the purification of Albumin & IgG, whereas the eluate from the same column is the starting material for the purification of Factor IX. If it is desired to purify Thrombin, then a second eluate from the same column could be used to obtain Thrombin. If it is desired to obtain alpha 1 proteinase inhibitor (A1Pi), then the flow through sample from the first anion exchange is further fractionated on the anion exchange column used for albumin and a second eluate is collected and so on. The integration of the process ensures that the processes for the purification of the individual proteins from a single plasma sample, are inter-dependent and none of the fractions containing a therapeutic protein gets wasted, thus ensuring optimal utilization of human plasma, which is a rare and precious commodity world-wide.

Purification of Factor VIII in the Integrated Process Scheme

Fraction 1 from the initial plasma fractionation-gel filtration step, containing Factor VIII and other high molecular weight proteins is the starting material for this purification process. This plasma fraction is further purified by loading on an anion exchange column packed with Q SEPHAROSER™ or any other anionic ion exchangers commercially available such as DEAE (Diethylaminoethyl), QAE (Diethyl (2-hydroxypropyl)ammonioethyl) or related resins known to people skilled in the art. The column is equilibrated with a buffer made from salts such as citrate or related salts such as acetate, in the molarity range of 0.005M to 0.1M containing NaCl in the range of 0.01M to 0.15M in a pH range of 5.5 to 8.0. The column is washed with the buffer and eluted using an elution buffer in the concentration range of 0.05M to 0.5M. The anion exchange eluate containing Factor VIII is subjected to a solvent-detergent (S/D) treatment that involves the addition of 0.3 to 0.5% w/w Tri-n-butyl phosphate (TNBP) and 1 to 2% w/w Tween 80 for a period of 12 hours at room temperature or around 24° C., for virus inactivation. The S/D treated sample is then loaded onto a cation exchange column to remove the viral inactivation reagents. The said cation exchange column is packed with SP SEPHAROSE™ (sulpho propyl sepharose) or CM SEPHAROSE™ (caboxymethyl sepharose) or related resins and equilibrated with sodium citrate (preferably 10 mM to 50 mM concentration) at a pH 5 to 7 and eluted with an equilibration buffer containing 0.1 to 1.5M sodium chloride or 0.4 to 1.0M calcium chloride or both. The eluate from this column is buffer exchanged into a formulation buffer and subjected to a second virus removal step by nanofiltration. This can be optionally loaded onto a gel filtration column containing separation media in the range for high molecular weight separations. The column can be run using the final formulation buffer. This helps in getting rid of any minor protein impurities in the sample containing Factor VIII and facilitates the exchange of the protein into the final formulation buffer.

This is subjected to a second virus removal step by nanofiltration using commercially available molecular size cut-off filters followed by a third viral inactivation step after filling the liquid into the vials, freeze drying and then subjecting it to heat treatment at 80° C. for 72 hours.

Fraction 2 from the initial plasma fractionation, namely, the gel filtration step which contains Fibrinogen along with certain classes of immunoglobulins, lipoproteins, transferrin and other proteins, is the starting plasma fraction for the purification of these therapeutic protein products.

Purification of Factor IX, IgG and Albumin in the Integrated Process Scheme

1. One of the said 3 fractions (Fraction 3) collected from the initial gel filtration separation of plasma is further fractionated by loading onto an anion exchange column like DEAE or Q Sepharose, more preferably DEAE or any similar weak anion exchangers.

2. This fraction 3 is allowed to pass through the above anion exchange column, which results in the binding of Factor IX, which is later eluted and the remaining two proteins IgG and Albumin are recovered in the unbound fraction. Factor IX is further purified by a two-step chromatography procedure.

3. The unbound (flow through) fraction containing IgG and albumin are further processed by dedicated chromatography steps to get therapeutic grade purity levels of IgG and albumin.

Anion Exchange Column Equilibration:

The anion exchange column like DEAE is equilibrated with acetate, citrate or any other anionic buffer salt of molarity 0.01 M to 0.15M in the pH range 6.5 to 8.0.

4. The flow through fraction that has albumin, IgG desalted by diafiltration or passing through a chromatography column 5. The euglobulins are removed by precipitation and this sample is used as the starting material for the purification of IgG and Albumin.

Fraction 3 from the initial plasma fractionation, namely, gel filtration step, containing IgG, Albumin, Factor IX, AT-III and other proteins is the starting plasma fraction for obtaining Factor IX, IgG and Albumin. This plasma fraction is loaded onto an anion exchange column such as DEAE SEPHAROSER® or Q SEPHAROSER® more preferably DEAE or any similar weak anion exchanger. This plasma fraction is allowed to pass through the above anion exchange column equilibrated with acetate, citrate or any other anionic buffer salt of molarity 0.01 M to 0.15M in the pH range 6.5 to 8.0 which results in the binding of Factor IX, which is eluted with a salt and the remaining two proteins—IgG and Albumin, are recovered in the unbound fraction. The elution of Factor IX is achieved by increasing the sodium chloride concentration to a range of 0.06M to 0.3M in the column equilibration buffer. The Factor IX in the eluate is further purified by a two-step chromatography procedure.

The unbound (flow through) fraction of the DEAE column containing IgG and albumin, is subjected to the removal of euglobulins by precipitation and this sample is then subjected to further purification to obtain purified IgG and Albumin. As is expected from an integrated process, this sample which is a mixture of IgG, Albumin and few other plasma proteins, when subjected to an anion exchange chromatography step, binds Albumin and not IgG to the column, thereby separating these two proteins and obtaining IgG in the flow through fraction. The anion exchange column is packed with DEAE or Q SEPHAROSER™ resin to a height ranging from 5 to 25 cm. This is equilibrated with a buffer of an acetate, a citrate or a phosphate salt in a concentration of 5 mM to 100 mM in a pH range of 4.0 to 7.0, more preferably in the range of 4.5 to 6.5. The elution is carried out with buffers preferably of the same salt in a concentration range of 50 mM to 200 mM and a pH range of 4.0 to 7.0. After the completion of this column step, Albumin is obtained as a major protein in the eluate with a few other protein impurities and IgG is obtained as a major protein in the flow through fraction. To obtain a therapeutic grade purity, it is necessary for these proteins to undergo just 1 or 2 polishing steps.

Desalting:

Desalting of the second lot of the sample is achieved by SEPHADEX G25™ chromatography using any anionic salt buffer such as sodium acetate buffer in the required pH range of 6.5 to 8.0; or by other methods such as diafiltration on a membrane filtration set-up. The desalted and concentrated sample is subjected to low pH precipitation for the removal of euglobulins.

The euglobulin precipitation step is carried out in the conductivity range of 0.5 mS to 5 mS, more preferably in the range of 0.6 mS to 4 mS and preferably in the pH range of 4 to 7. The plasma sample under these conditions is held at a temperature between 2 to 20 degrees centigrade, for a time of 2 hrs to 16 hrs. The euglobulin pellet obtained after this step has a weight of about 20-45 gm/L of plasma.

The supernatant sample after removal of euglobulin pellet is again loaded on an ion exchange column, more preferably a second anion exchange column such as DEAE SEPHAROSER® Q SEPHAROSER® or equivalent to enable separation of the albumin and IgG from the load sample.

Column Setup:

The column has a height ranging from 5 and 25 cm and the column is equilibrated with a buffer made from salts such as acetate, citrate or phosphate at concentration ranges from 5 mM to 100 mM in the pH range of 4.0 to 7.0, more preferably in the range of 4.5 to 6.5. The elution is carried out with buffers preferably of the same salt in the concentration range of 50 mM to 200 mM, in the pH range of 4.0 to 7.0.

The elution peak fraction obtained contains albumin as the major protein, while the flow through fraction contains IgG and thus these two different fractions are processed separately for further purification.

Purification of IgG

The flow through fraction containing IgG as the major protein from the above DEAE step is loaded onto an anion exchange column such as Q SEPHAROSER® although DEAE, TMAE or any other anionic resins from commercial vendors can also be used) to remove the minor protein impurities before being subjected to the viral inactivation steps that are necessary for therapeutic administration.

An anion exchange column of height ranging from 5 cm to 20 cm is packed and the column is equilibrated with a buffer of acetate, citrate, phosphate or any other suitable anionic salt with a molarity in the range of 5 mM to 100 mM, more preferably in the range of 10 mM to 60 mM, and of pH in the range of 5 to 8, more preferably between 5.5 and 7.5.

The IgG containing fraction is collected as flow through fraction from this column is subjected to low pH treatment for 12 to 16 hrs, followed by a solvent-detergent (S/D) treatment for virus inactivation of enveloped viruses at 30° C., more preferably at 25° C. to 32° C., for 4 to 16 hrs.

The chemicals used for S/D are 1% w/w TNBP (tri-n-butyl phosphate) and 1% w/w Triton X-100. After incubation, the chemicals used for S/D are removed by loading on a cation exchange column such as SP SEPHAROSE™ or CM SEPHAROSE™ equilibrated in 5 to 50 mM sodium acetate or citrate at pH 4.0 to 6.0 and eluting with buffer containing glycine and NaCl in the concentration range of 0.1 to 0.5 M.

This sample is then passed through a nanofilter to remove other non-enveloped viruses before being subjected to ultrafiltration and diafiltration steps for exchanging into the final formulation buffer for sterile filtration and filling in vials.

The solvent-detergent solution addition is done with 1% w/w TNBP (tri-n-butyl phosphate) and 1% w/w Triton X-100, the concentrations required for viral inactivation. The final IgG sample obtained by this process has the required purity (Protein composition >96% by Zone Electrophoresis), efficacy (Fc function >60%) and safety profile (Anti-complementary activity <50%, IgA antibodies <4 mg/L, Anti-A & Anti-B hemagglutinins not detectable, IgM <0.1 mg/mL) required for intravenous administration (FIG. 5: Table 2).

Figure 2:
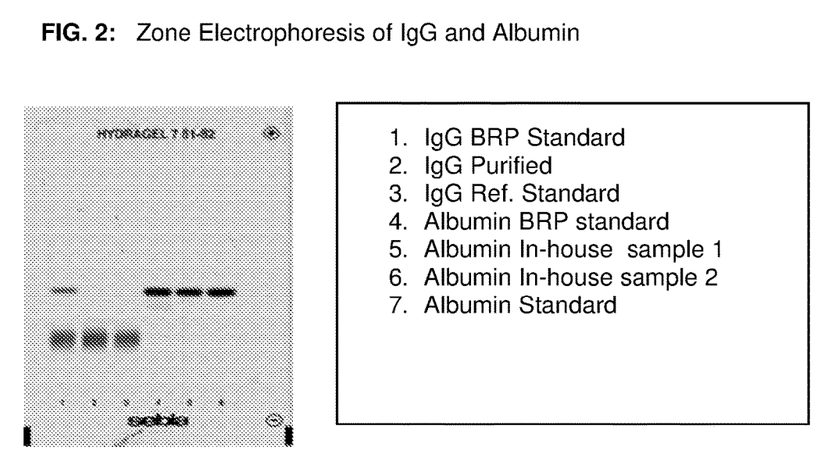
FIG. 2 is a representation of Zone Electrophoresis of IgG and Albumin.
Figure 3A:
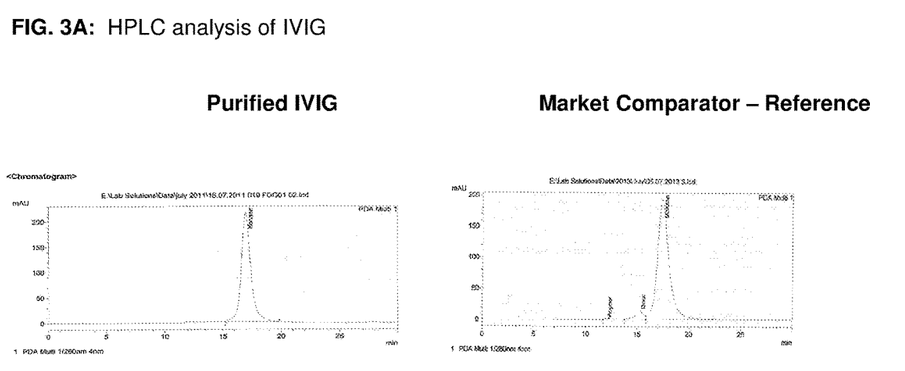
FIG. 3A represents the High-performance liquid chromatography (HPLC) analysis of IVIG.
Figure 6:
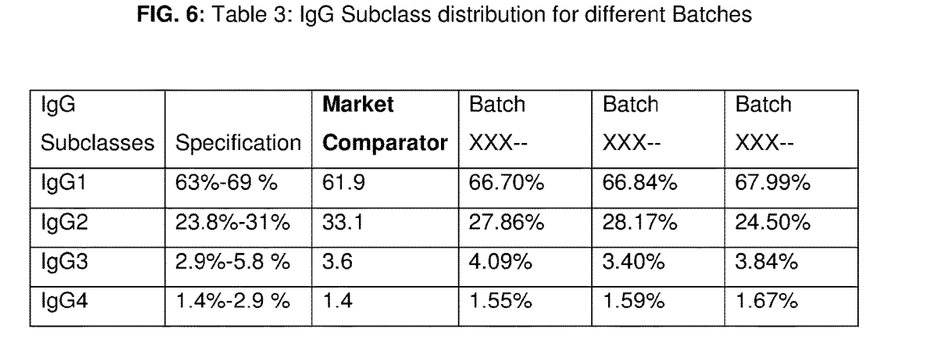
FIG. 6: Table 3: IgG subclass distribution for different batches
Figure 7:
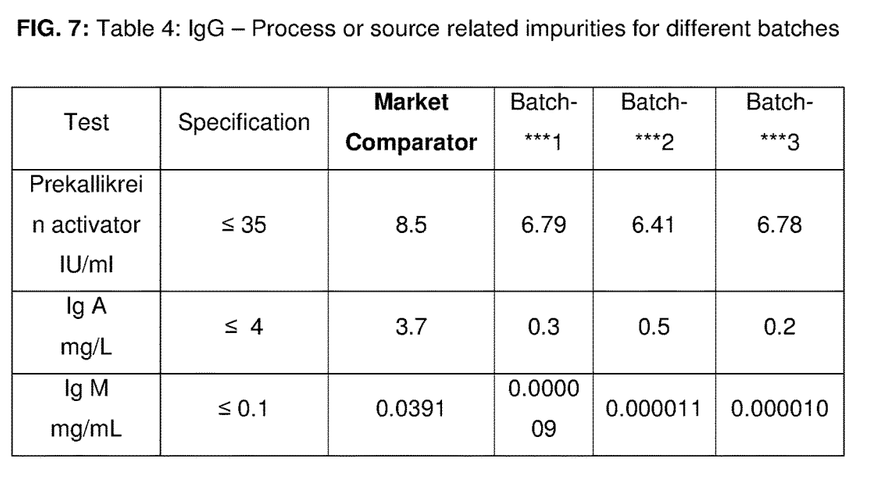
FIG. 7: Table 4: IgG—Process or source related impurities for different batches

The manufacturing process of IgG described above doesn't compromise on the biological activity of the IgG molecules. They are highly pure (FIG. 3A), functionally intact with normal IgG sub-class distribution and effector functions. The preparations are also safe with regard to pathogen safety and product and process related impurities. The protein composition, by Zone electrophoresis, expected as per pharmacopoeial guidelines is IgG >96% and other contaminant proteins <4%. But the protein composition of the present invention, is IgG=100% as per Zone electrophoresis with 0% contaminant proteins (FIG. 2). The distribution of isoforms IgG1 (63% to 69%), IgG2 (23% to 31%), IgG3 (2.9% to 5.8%), IgG4 (1.4% to 2.9%) within the range matching the normal plasma levels of these isoforms. These results were tabulated in FIG. 6: Table 3 (IgG Subclass distribution for different Batches). Levels of process related contaminants such as prekallikrein activator is 7.4 IU/ml, the activated coagulation factors have >400 sec clotting time, IgA is 0.5 mg and IgM is 0.000009 mg/mL. These results were tabulated in FIG. 7: Table 4 (IgG—Process or source related impurities for different batches). The IgG preparation described herein has an average index function Fc greater than 80%. This demonstrates that the disclosed process for IgG preparation in the present invention retains the effector functions and is biologically active.

Polishing Steps in Purification of Albumin for Therapeutic Grade Purity

The eluate from the second DEAE SEPHAROSE™ column (described in IgG section above) is loaded onto a cation exchange column such as CM SEPHAROSE™ (although other cationic exchangers like SP or equivalent may also be used). The CM SEPHAROSE™ column is equilibrated with a buffer of an acetate, a citrate or a phosphate at a concentration of 10 mM to 100 mM in the pH range of 4 to 6. The albumin with some protein impurities, is bound to the column, which is then eluted with the same buffer containing NaCl in the range of 25 mM to 0.2M, in the same pH range. The virus inactivation is carried out by the addition of caprylic acid at a pH of 4.0 to 4.5 for 10 to 12 hours.

After virus inactivation treatment, the albumin sample is subjected to heat treatment at a temperature of 45° C.-65° C., more preferably 50° C.-60° C., for a period of 1 hr to 10 hrs, more preferably 2 hrs to 6 hrs, and then subjected to filtration. The precipitates obtained are removed by filtration and the clear filtrate is formulated after exchanging into the formulation buffer.

The filtrate obtained is diafiltered and concentrated before the addition of formulation excipients. The final formulated sample also contains 16 mM each of N-acetyl tryptophanate and sodium caprylate. The formulated Albumin solution is pasteurized at 60° C. for 10 to 12 hours for virus inactivation, filled into vials aseptically, and subjected to a second round of pasteurization.

This formulated bulk solution is filled aseptically in vials, stoppered, sealed and then subjected to a second round of pasteurization at conditions similar to the initial pasteurization.

Figure 3B:
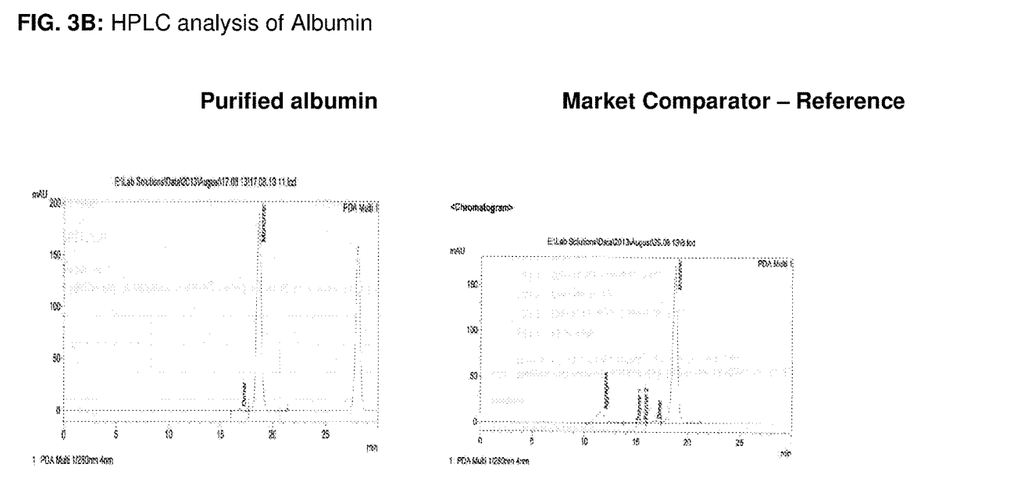
FIG. 3B represents the HPLC analysis of Albumin.
Figure 8:
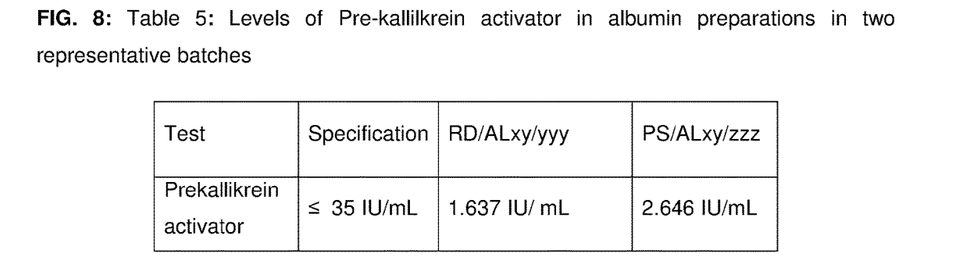
FIG. 8: Table 5: Levels of Pre-kallilkrein activator in albumin preparations in two representative batches
Figure 9:
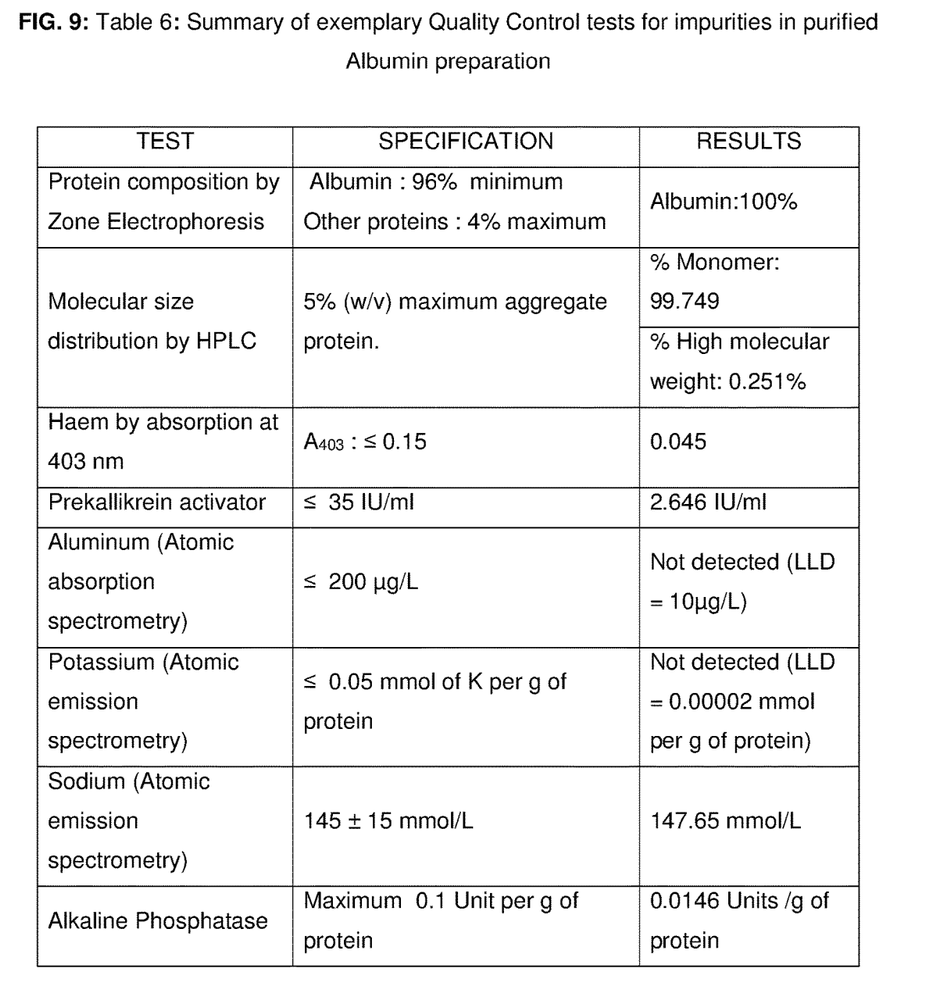
FIG. 9: Table 6: Summary of exemplary Quality Control tests for impurities in purified Albumin preparation

In the present invention, the process for the isolation and purification albumin allows albumin to be purified to near homogeneity and predominantly in the monomeric form, with aggregate levels not exceeding 0.5% (FIG. 3B). This is ten-fold lower than that stated in the pharmacopoeia, where the specification limit for aggregates is expected to be not greater than 5%. The albumin preparation is purified to near homogeneity that is apparent from detection of only one principal band of 100% albumin in the electropherogram when investigated using Zone Electrophoresis method (FIG. 2). The limit specified in the monograph allows not more than 5% of bands other than the principal band. According to this invention, there are no additional protein bands and the principal albumin band makes up 100% of the protein present in the sample. Very low levels of prekallikrein activator contaminant in albumin preparation were observed with prekallikrein activator being about fifteen-fold lower than the pharmacopoeial limit as determined by the assay described in the E. P. monograph. The limit set for this impurity is <35 IU/ml and the said albumin preparation contains prekallikrein contaminant less than 3 IU/mL (FIG. 8 Table 5). The albumin solution also has very low levels of metal ions like aluminium (below LLD 10 ppb) and potassium (below LLD of 0.00002 mmol per gm of protein) as determined by atomic absorption spectrometry. The pharmacopoeial limit is set to not exceed 200 ppb for Aluminium and ≤0.05 mmol of Potassium per gm of protein. These results were tabulated in FIG. 9: Table 6 (Summary of a few major QC tests for impurities in purified Albumin preparation). These results show that the said albumin preparation is very pure and devoid of other plasma proteins and process related contaminants.

Polishing Steps in Purification of Factor IX for Therapeutic Grade Purity

The final steps in the purification of Factor IX is achieved from the eluate fraction of the first anion exchange—DEAE SEPHAROSER™ column (described in section on 'Purification of Factor IX, IgG and Albumin in the Integrated process scheme') where the Factor IX protein is recovered in the eluate fraction by sodium chloride in the range of 0.06M to 0.3M at the same pH. This eluate is subjected to viral inactivation by addition of Solvent-Detergent (S/D) chemicals, 0.8 to 1.2% Tween-80 and 0.2 to 0.5% TNBP (tri-n-butyl phosphate) and incubating at room temperature for 4 to 16 hours at pH 4.0. The viral inactivated Factor IX sample is then loaded on a metal chelate or HEPARIN SEPHAROSE™ affinity column to get rid of the S/D chemicals and impurities such as prothrombin and C1 esterase inhibitor and to collect Factor IX that is bound to the column. If a Heparin affinity column is used, it is equilibrated with sodium citrate buffer of a concentration of 0.01 M to 0.1 M in the pH range of 5.0 to 9.0 containing 1 to 20 mM calcium chloride. The column is eluted by increasing the sodium chloride from 0.05M to 1.5 M in the same equilibration buffer. The Factor IX obtained after this step is relatively pure but can optionally be loaded on a gel filtration column to obtain even greater purity. The gel filtration chromatography column is packed with resins such as SEPHADEX™ SUPEROSE™, SUPERDEX™ or SEPHACRYL™ in a separation range of 10 KD to 600 KD, equilibrated with buffers containing sodium salts of citrate or acetate in the molarity range of 5 mM to 100 mM and a pH in the range of 6.0 to 8.0. The Factor IX sample is eluted as a peak which is collected and subjected to concentration and nanofiltration to remove viruses. This purified Factor IX sample is sterile filtered, filled in vials and lyophilized for therapeutic administration.

Figure 4:
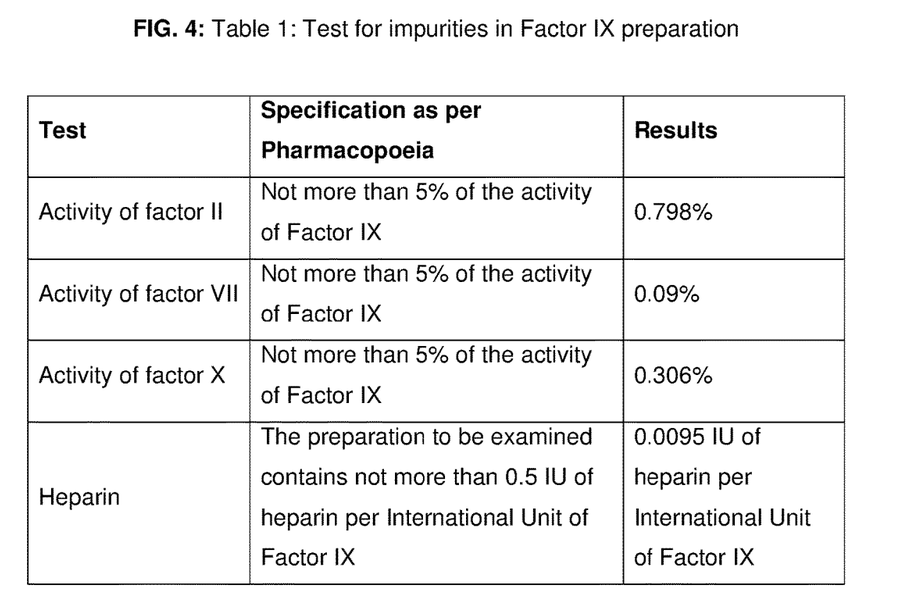
FIG. 4: Table 1: Test for impurities in Factor IX preparation

The chromatography based process for the production of Factor IX gives a preparation of Factor IX with specific activity of ≥200 IU/mg. This preparation also has impurity levels many fold lesser than the limits specified by the regulatory authorities. The main contaminants in Factor IX are Factor II (the level in the preparation of the present invention is less than 1% against the regulatory limit of <5%), Factor VII (the level in the preparation of the present invention is around 0.1% against the regulatory limit of <5%), Factor X (the level in our preparation is around 0.3% against the regulatory limit of <5%). The contaminating levels of Heparin in the Factor IX preparation is less than 0.001 IU/IU of Factor IX against the regulatory specified limit of "not to exceed 0.5 IU" of Heparin per IU of Factor IX. These results are presented in FIG. 4: Table 1 (Test for impurities in Factor IX preparation).

The present invention is not limited to the products specified in the embodiments, but has the potential to purify several other plasma products by incorporating minor variations in the wash and elution conditions. By circumventing the ethanol precipitation steps mentioned in the Cohn's method of fractionation, the purification scheme of the present invention saves on the use of several thousands of liters of ethanol, a reagent that requires explosion-proof manufacturing facilities, affects protein quality (more aggregates and denaturants), activity (lower potency) and yield (lower recoveries). The quality control tests on the plasma products purified by this scheme show that the products fulfill the quality control specifications exceedingly well.

The invention claimed is:

1. An integrated process for the isolation and purification of plasma derived clotting Factor VIII, clotting Factor IX, albumin and immunoglobulin (IgG), without the use of ethanol precipitation, comprising:
   a) subjecting plasma to gel filtration chromatography to obtain three fractions (Fraction I, Fraction II and Fraction III);
   b) subjecting Fraction I and Fraction III to further chromatographic separations using anion and cation exchange resins; and
   c) subjecting to viral inactivation and recovering isolated and purified clotting Factor VIII from Fraction I, and clotting Factor IX, albumin and immunoglobulin (IgG) from Fraction III.

2. The process of claim 1, wherein isolating and purifying clotting Factor VIII from said Fraction I, further comprises loading onto a cation exchange column to remove the viral inactivation reagents after solvent-detergent (S/D) treatment followed by nanofiltration, freeze drying, and heat treatment at 80° C. for 72 hours.

3. The process of claim 1, wherein the isolated and purified clotting Factor IX, albumin and IgG are obtained by fractionation of Fraction III using an anion exchange column, resulting in a bound fraction containing Factor IX, and recovering IgG and albumin from the unbound fraction.

4. The process of claim 3, wherein Factor IX is obtained from the bound fraction, comprising:
   i) subjecting said bound fraction to a solvent-detergent (S/D) treatment under standard conditions for viral inactivation;
   ii) loading on an affinity or metal chelate chromatography column to specifically bind the clotting Factor IX; and
   iii) subjecting ii) to a gel filtration chromatography step followed by nanofiltration for viral removal.

5. The process of claim 3, wherein albumin is obtained from the unbound fraction, comprising:
   i) loading said unbound fraction containing albumin and IgG on an anion exchange column to obtain an eluate containing albumin and an unbound fraction containing IgG, and further loading the eluate on a cation exchange column to elute the albumin containing fraction;
   ii) subjecting said eluate to viral inactivation after addition of caprylate and incubating it at a low pH of 4.5 for 10-12 hours;
   iii) concentrating and subjecting ii) to heat treatment at a range of 50° C.-60° C., for a period of 2 to 6 hours followed by filtration to obtain a filtrate; and
   iv) concentrating the filtrate, adding formulation excipients and pasteurizing at 60° C. for 10 hours for viral inactivation.

6. The process of claim 5, wherein IgG is obtained from the unbound fraction, comprising:
   i) loading said unbound fraction containing IgG to an anion exchange column chromatography;
   ii) subjecting said unbound fraction containing IgG further to a low pH treatment for 12-16 hours followed by viral inactivation through a solvent-detergent (S/D) treatment at 25° C. to 32° C. for 4 to 16 hours; and
   iii) loading said fraction on a cation exchange column to collect the eluate containing IgG, further passing it through a nanofilter to obtain a filtrate, subjecting said filtrate to a series of diafiltration steps to concentrate the filtrate, and formulating by adding excipients.

* * * * *